US011627941B2

(12) United States Patent
Halmann et al.

(10) Patent No.: US 11,627,941 B2
(45) Date of Patent: Apr. 18, 2023

(54) METHODS AND SYSTEMS FOR DETECTING PLEURAL IRREGULARITIES IN MEDICAL IMAGES

(71) Applicant: GE Precision Healthcare LLC, Milwaukee, WI (US)

(72) Inventors: Menachem Halmann, Monona, WI (US); Dani Pinkovich, Brookline, MA (US); Carmit Shiran, Haifa (IL); Robert John Anderson, Oshkosh, WI (US); Antonio Fabian Fermoso, Madrid (ES); Cynthia Owen, Powhatan, AR (US)

(73) Assignee: GE Precision Healthcare LLC, Milwaukee, WI (US)

( * ) Notice: Subject to any disclaimer, the term of this patent is extended or adjusted under 35 U.S.C. 154(b) by 212 days.

(21) Appl. No.: 17/005,153

(22) Filed: Aug. 27, 2020

(65) Prior Publication Data
US 2022/0061813 A1    Mar. 3, 2022

(51) Int. Cl.
*A61B 8/00* (2006.01)
*A61B 5/08* (2006.01)
(Continued)

(52) U.S. Cl.
CPC ............ *A61B 8/469* (2013.01); *A61B 5/055* (2013.01); *A61B 5/08* (2013.01); *A61B 5/7425* (2013.01);
(Continued)

(58) Field of Classification Search
CPC ........... A61B 8/469; A61B 5/055; A61B 5/08; A61B 5/7425; A61B 5/7485; A61B 6/032;
(Continued)

(56) References Cited

U.S. PATENT DOCUMENTS

2016/0239959 A1* 8/2016 Blackbourne .......... G06V 10/40
2018/0181828 A1* 6/2018 Sakamoto ............ G06V 10/44
(Continued)

FOREIGN PATENT DOCUMENTS

EP    3482689 A1 *  5/2019  ............. A61B 8/085
EP    3682811 A1 *  7/2020  ............. A61B 8/085
(Continued)

OTHER PUBLICATIONS

Clevert D.A., "Lung ultrasound in patients with coronavirus COVID-19 disease," (Apr. 14, 2020) SIEMENS, <https://www.siemens-healthineers.com/ultrasound/lung-ultrasound-covid-19> & <https://pep.siemens-info.com/en-us/lung-ultrasound-in-patients-with-coronavirus-covid-19-disease>. (Year: 2020).*

(Continued)

*Primary Examiner* — Joel Lamprecht
*Assistant Examiner* — Ashish S Jasani
(74) *Attorney, Agent, or Firm* — McCoy Russell LLP

(57) ABSTRACT

Various methods and systems are provided for a medical imaging system. In one embodiment, a method includes acquiring a series of medical images of a lung, identifying a pleural line in each medical image of the series, evaluating the pleural line for irregularities in each medical image of the series, and outputting an annotated version of each medical image of the series, the annotated version including visual markers for healthy pleura and irregular pleura. In this way, an operator of the medical imaging system may be alerted to pleural irregularities during a scan.

19 Claims, 10 Drawing Sheets

(51) Int. Cl.

| | | |
|---|---|---|
| *A61B 5/00* | (2006.01) | |
| *A61B 6/03* | (2006.01) | |
| *A61B 8/08* | (2006.01) | |
| *G06T 7/00* | (2017.01) | |
| *A61B 5/055* | (2006.01) | |
| *A61B 6/00* | (2006.01) | |
| *G06T 7/13* | (2017.01) | |
| *G06T 3/40* | (2006.01) | |
| *G06T 19/00* | (2011.01) | |

(52) U.S. Cl.
CPC ............ *A61B 5/7485* (2013.01); *A61B 6/032* (2013.01); *A61B 6/037* (2013.01); *A61B 6/463* (2013.01); *A61B 6/469* (2013.01); *A61B 6/50* (2013.01); *A61B 6/5217* (2013.01); *A61B 6/5235* (2013.01); *A61B 6/5247* (2013.01); *A61B 8/08* (2013.01); *A61B 8/0858* (2013.01); *A61B 8/463* (2013.01); *A61B 8/466* (2013.01); *A61B 8/468* (2013.01); *A61B 8/5223* (2013.01); *A61B 8/5246* (2013.01); *A61B 8/5253* (2013.01); *A61B 8/5261* (2013.01); *G06T 3/4038* (2013.01); *G06T 7/0012* (2013.01); *G06T 7/13* (2017.01); *G06T 19/00* (2013.01); *G06T 2207/10136* (2013.01); *G06T 2207/20221* (2013.01); *G06T 2207/30061* (2013.01)

(58) Field of Classification Search
CPC ......... A61B 6/037; A61B 6/463; A61B 6/469; A61B 6/50; A61B 6/5217; A61B 6/5235; A61B 6/5247; A61B 8/08; A61B 8/463; A61B 8/5223; A61B 8/5246; A61B 8/5261; G06T 3/4038; G06T 7/0012; G06T 7/13; G06T 19/00; G06T 2207/10136; G06T 2207/20221; G06T 2207/30061

See application file for complete search history.

(56) References Cited

U.S. PATENT DOCUMENTS

2019/0000425 A1* 1/2019 Hu .................... G06T 7/0012
2020/0054306 A1* 2/2020 Mehanian ................ G06T 7/70

FOREIGN PATENT DOCUMENTS

RU       2729368 C1    8/2020
WO     WO-2019101714 A1 *  5/2019 ............. A61B 8/085

OTHER PUBLICATIONS

Clevert D.A., "Lung ultrasound in patients with coronavirus COVID-19 disease," (Jun. 4, 2020) SIEMENS, <https://www.youtube.com/watch?v=Xr6_fySDpt8>. (Year: 2020).*

Goodman et al., "Ultrasound detection of pneumothorax," (Nov. 1999) Clinical Radiology, vol. 54, Issue 11, Nov. 1999, pp. 736-739. (Year: 1999).*

Carrer, L. et al., "Automatic Pleural Line Extraction and COVID-19 Scoring from Lung Ultrasound Data," IEEE Transactions on Ultrasonics, Ferroelectrics and Frequency Control, Jun. 29, 2020, 11 pages.

* cited by examiner

METHODS AND SYSTEMS FOR DETECTING PLEURAL IRREGULARITIES IN MEDICAL IMAGES

FIELD

Embodiments of the subject matter disclosed herein relate to ultrasound imaging.

BACKGROUND

An ultrasound imaging system typically includes an ultrasound probe that is applied to a patient's body and a workstation or device that is operably coupled to the probe. During a scan, the probe may be controlled by an operator of the system and is configured to transmit and receive ultrasound signals that are processed into an ultrasound image by the workstation or device. The workstation or device may show the ultrasound images as well as a plurality of user-selectable inputs through a display device. The operator or other user may interact with the workstation or device to analyze the images displayed on and/or select from the plurality of user-selectable inputs.

As one example, ultrasound imaging may be used for examining a patient's lungs due to an ease of use of the ultrasound imaging system at a point-of-care and low cost relative to a chest x-ray or a chest computed tomography (CT) scan, for example. Further, the ultrasound imaging system does not expose the patient to radiation. Lung ultrasound imaging, also termed lung sonography, includes interpreting ultrasound artifacts for diagnostic purposes. The ultrasound artifacts include A-lines, which are substantially parallel and horizontal repeating lines caused by oscillating sound waves at pleura of the lungs, and B-lines, which are substantially vertical "comet-tail" artifacts of hyperechoic echoes indicating various lung pathologies including the presence of fluid.

BRIEF DESCRIPTION

This summary introduces concepts that are described in more detail in the detailed description. It should not be used to identify essential features of the claimed subject matter, nor to limit the scope of the claimed subject matter.

In one aspect, a method can include acquiring a series of medical images of a lung, identifying a pleural line in each medical image of the series, evaluating the pleural line for irregularities in each medical image of the series, and outputting an annotated version of each medical image of the series, the annotated version including visual markers for healthy pleura and irregular pleura.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 5:
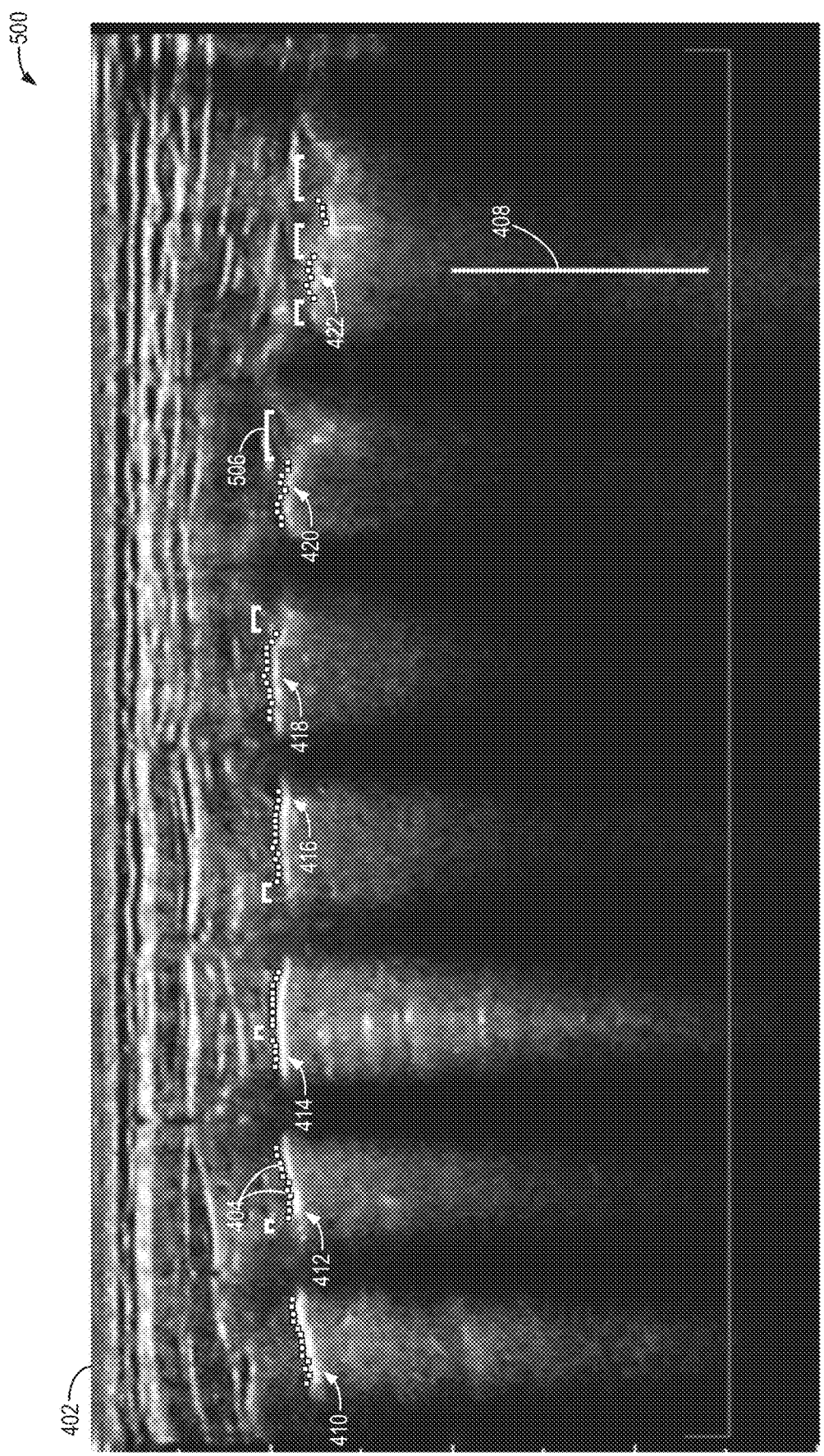
FIG. 5 shows a second example annotated panoramic lung ultrasound image that may be output to a display, according to an embodiment.
Figure 6A:
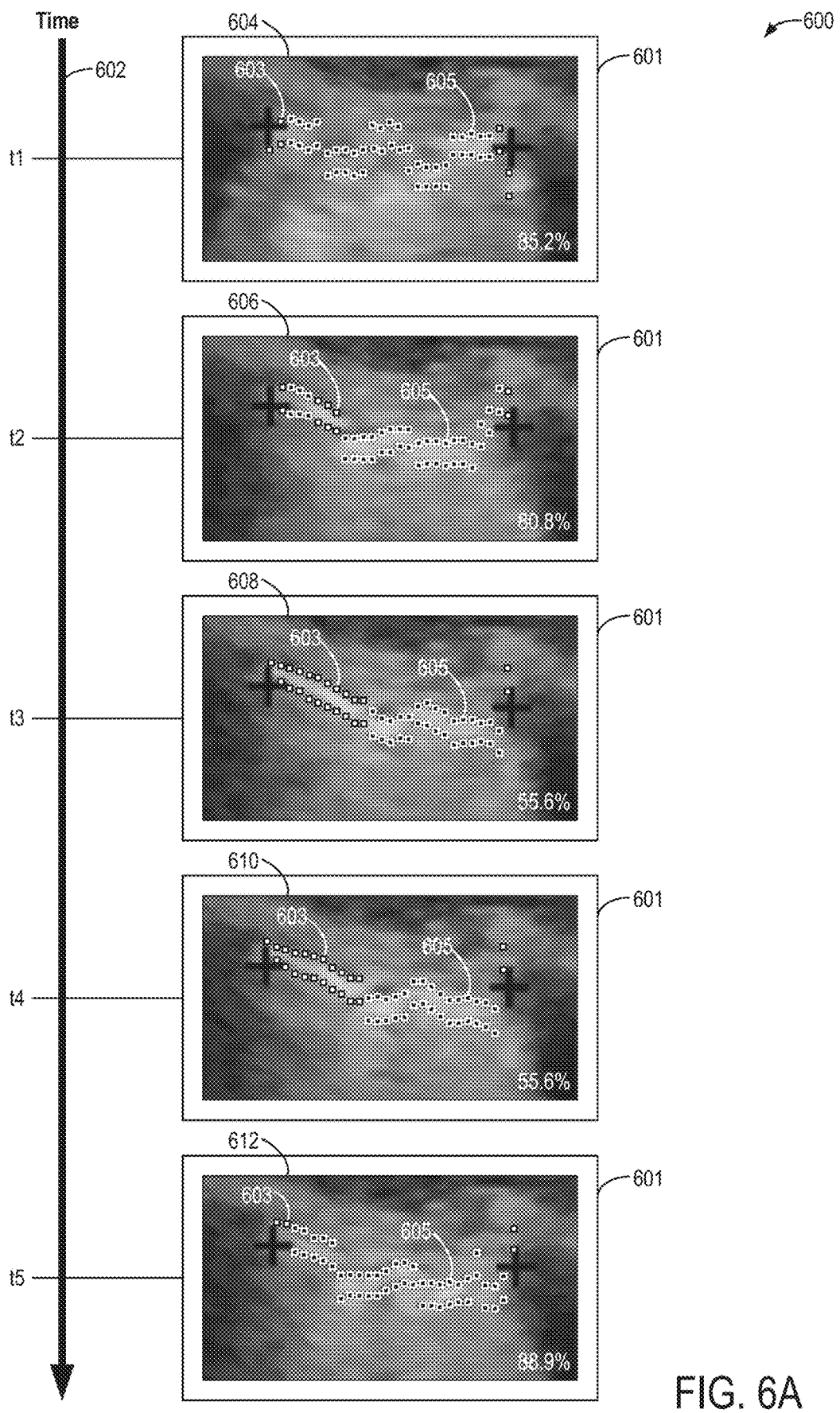
FIGS. 6A and 6B show a first example sequence of display outputs that may occur during and following a lung ultrasound, according to an embodiment.

Embodiments of the present disclosure will now be described, by way of example, with reference to the FIGS. 1-8, which relate to various embodiments for automatically detecting pleural irregularities based on medical imaging data acquired by an imaging system, such as the ultrasound imaging system shown in FIG. 1. As the processes described herein may be applied to pre-processed imaging data and/or to processed images, the term "image" is generally used throughout the disclosure to denote both pre-processed and partially-processed image data (e.g., pre-beamformed RF or I/Q data, pre-scan converted RF data) as well as fully processed images (e.g., scan converted and filtered images ready for display). An example image processing system that may be used to detect the pleural irregularities is shown in FIG. 2. The image processing system may employ image processing techniques and one or more algorithms to detect the pleural irregularities and output an indication of the detected pleural irregularities to an operator, such as according to the method of FIG. 3. Various visual markers or indicators may be used to distinguish healthy pleura from irregular pleura, such as illustrated in FIGS. 5 and 6. As depicted by the example display outputs in FIGS. 6A-7B, the pleural irregularities may be detected and scored in real-time, and then the system may select a best-frame representation for extended display. Further, the system may output information regarding a potential diagnosis or detected pathologies to the display. In some examples, a three-dimensional lung model also may be generated and output to the display, with the best-frame representation overlaid in an anatomically and spatially relevant position, such as shown in FIG. 8. In this way, pleural irregularities may be detected and quantified from ultrasound imaging data in real-time, decreasing a time until a diagnosis can be made and decreasing both intra-operator and inter-operator variation.

Advantages that may be realized in the practice of some embodiments of the described systems and techniques are that inconsistencies in the detection of pleural irregularities, particularly between different operators, may be decreased. This may be particularly advantageous for increasing a detection accuracy of point-of-care ultrasound operators, who may have less training than ultrasound experts (e.g., sonographers or radiologists). For example, an emergency room physician, who may not receive expert-level ultrasound training, may be more likely to overlook an irregularity or incorrectly identify a normal structure or an imaging artifact as an irregularity, which may increase a burden on a radiology department for follow up scans and increase patient discomfort. Further, by decreasing follow up scans and a mental burden on the point-of-care ultrasound operator, an amount of time until an accurate diagnosis is made may be decreased. Further still, the described system and techniques may include outputting a "best-frame" image of any lung pathology present by selecting an image showing a greatest occurrence of pleural irregularities and outputting a suggested diagnosis, further reducing the mental burden on the ultrasound operator and/or other clinicians involved in diagnosing and treating the patient being scanned.

Although the systems and methods described below for evaluating medical images are discussed with reference to an ultrasound imaging system, it may be noted that the methods described herein may be applied to a plurality of imaging systems (e.g., MRI, PET, x-ray, CT, or other similar systems).

Figure 1:
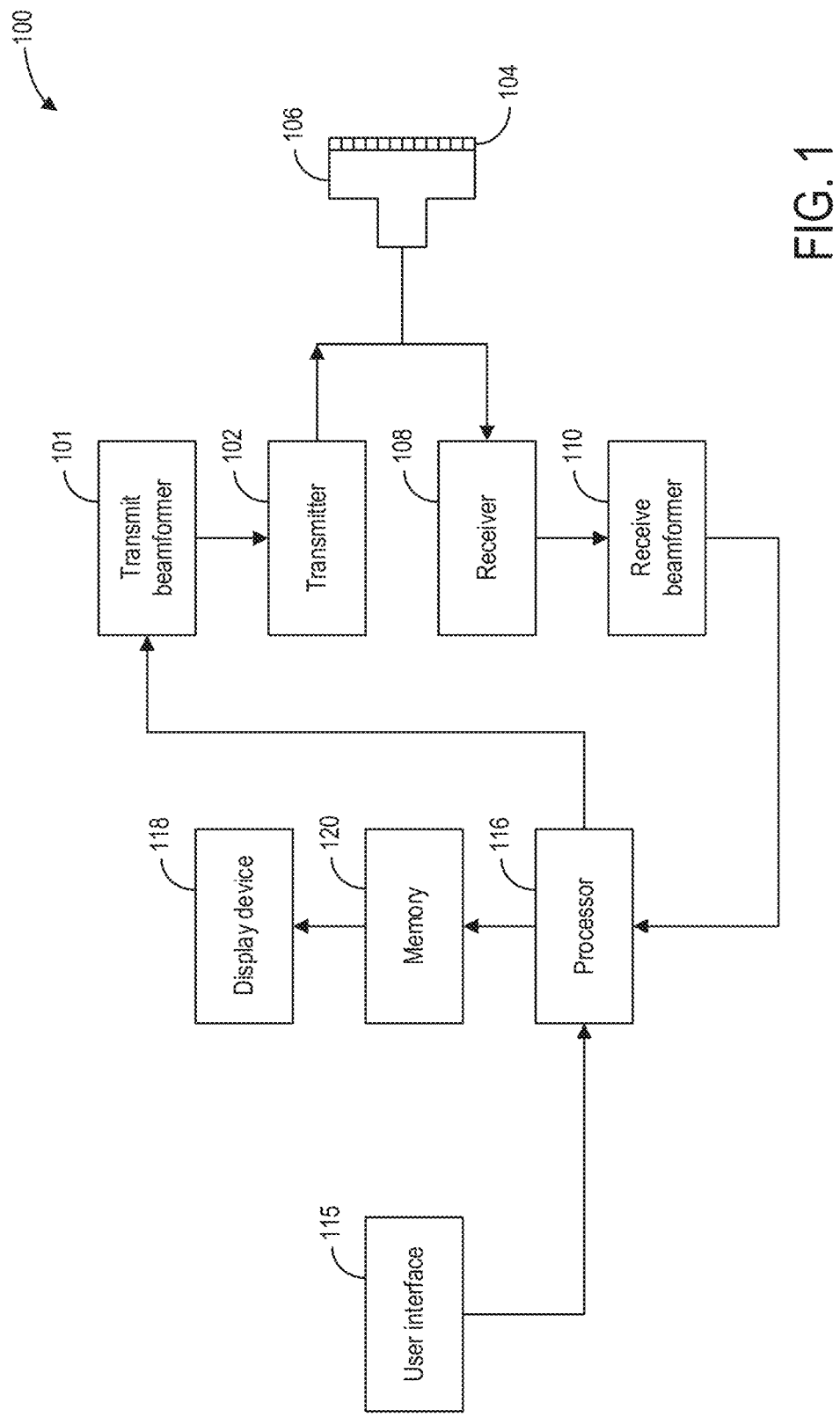
FIG. 1 shows a block schematic diagram of an ultrasound imaging system, according to an embodiment.
Figure 2:
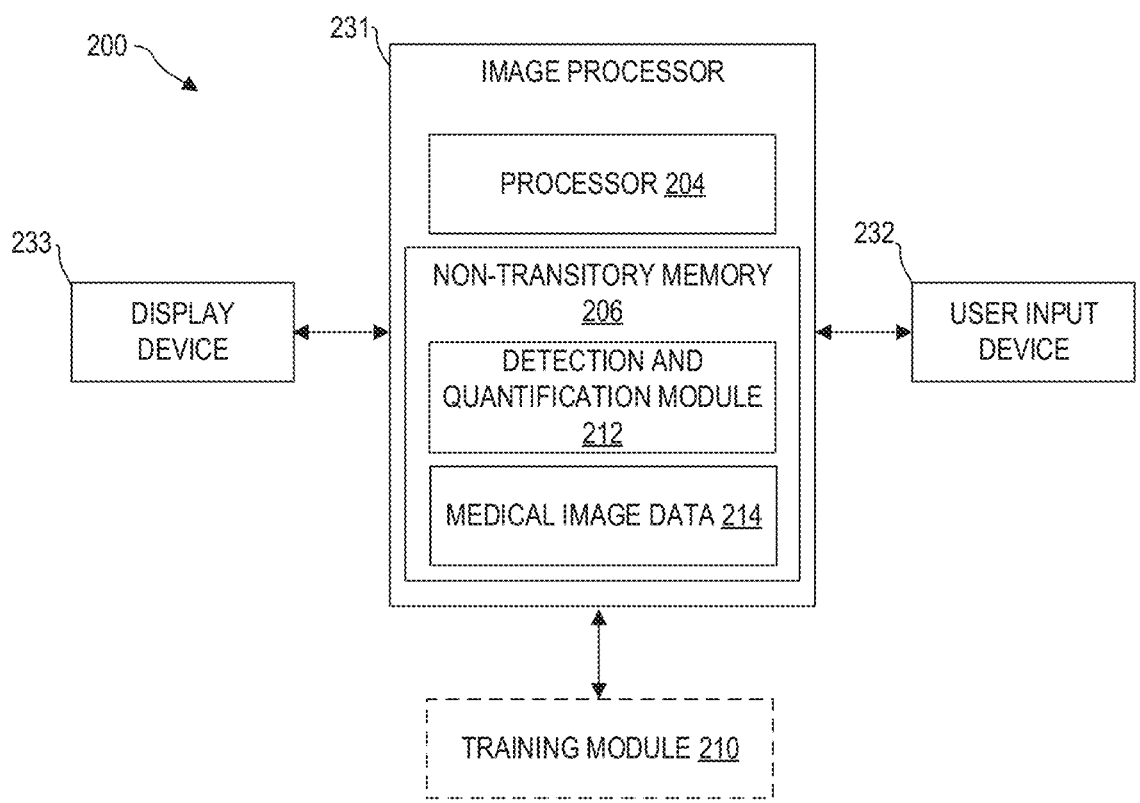
FIG. 2 is a schematic diagram illustrating an image processing system for detecting and classifying abnormalities in medical images, according to embodiment.

Referring to FIG. 1, a schematic diagram of an ultrasound imaging system 100 in accordance with an embodiment of the disclosure is shown. However, it may be understood that embodiments set forth herein may be implemented using other types of medical imaging modalities (e.g., magnetic resonance imaging, computed tomography, positron emission tomography, and so on). The ultrasound imaging system 100 includes a transmit beamformer 101 and a transmitter 102 that drives elements (e.g., transducer elements) 104 within a transducer array, herein referred to as a probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. The transducer elements 104 may be comprised of a piezoelectric material. When a voltage is applied to the piezoelectric material, the piezoelectric material physically expands and contracts, emitting an ultrasonic spherical wave. In this way, the transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104, and the electrical signals are received by a receiver 108. The electrical signals representing the received echoes are passed through a receive beamformer 110 that performs beamforming and outputs ultrasound data, which may be in the form of a radiofrequency (RF) signal. Additionally, the transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be positioned within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system.

A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of a rotary element, a mouse, a keyboard, a trackball, hard keys linked to specific actions, soft keys that may be configured to control different functions, and a graphical user interface displayed on a display device 118. In some embodiments, the display device 118 may include a touch-sensitive display, and thus, the display device 118 may be included in the user interface 115.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. As used herein, the term "electronic communication" may be defined to include both wired and wireless communications. The processor 116 may control the probe 106 to acquire data according to instructions stored on a memory of the processor and/or a memory 120. As one example, the processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processing unit (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay (e.g., substantially at the time of occurrence). For example, an embodiment may acquire images at a real-time rate of 7-20 frames/sec. The ultrasound imaging system 100 may acquire two-dimensional (2D) data of one or more planes at a significantly faster rate. However, it should be understood that the real-time frame-rate may be dependent on a length (e.g., duration) of time that it takes to acquire and/or process each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec.

In some embodiments, the data may be stored temporarily in a buffer (not shown) during a scanning session and processed in less than real-time in a live or off-line operation. Some embodiments of the disclosure may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example, by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 may store processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, elastography, tissue velocity imaging, strain, strain rate, and the like) to form 2D or three-dimensional (3D) images. When multiple images are obtained, the processor 116 may also be configured to stabilize or register the images. For example, one or more modules may generate B-mode, color Doppler, M-mode, color M-mode, color flow imaging, spectral Doppler, elastography, tissue velocity imaging (TVI), strain, strain rate, and the like, and combinations thereof. As one example, the one or more modules may process color Doppler data, which may include traditional color flow Doppler, power Doppler, high-definition (HD) flow Doppler, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real-time while a procedure (e.g., ultrasound imaging) is being performed on a patient. The video processor module may include a separate image memory, and the ultrasound images may be written to the image memory in order to be read and displayed by the display device 118.

Further, the components of the ultrasound imaging system 100 may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as the probe 106 and the user interface 115. Optionally, the ultrasound imaging system 100 may be a unitary system that is capable of being moved (e.g., portably) from room to room. For example, the ultrasound imaging system 100 may include wheels or may be transported on a cart, or may comprise a handheld device.

For example, in various embodiments of the present disclosure, one or more components of the ultrasound imaging system 100 may be included in a portable, handheld ultrasound imaging device. For example, the display device 118 and the user interface 115 may be integrated into an exterior surface of the handheld ultrasound imaging device, which may further contain the processor 116 and the memory 120 therein. The probe 106 may comprise a handheld probe in electronic communication with the handheld ultrasound imaging device to collect raw ultrasound data. The transmit beamformer 101, the transmitter 102, the receiver 108, and the receive beamformer 110 may be included in the same or different portions of the ultrasound imaging system 100. For example, the transmit beamformer 101, the transmitter 102, the receiver 108, and the receive beamformer 110 may be included in the handheld ultrasound imaging device, the probe, and combinations thereof.

Referring to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), an MRI system, a CT system, a single-photon emission computed tomography (SPECT) system, etc. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine-readable instructions stored in non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a field-programmable gate array (FPGA), or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a detection and quantification module 212 and medical image data 214. The detection and quantification module 212 includes one or more algorithms to process input medical images from the medical image data 214. Specifically, the detection and quantification module 212 may identify an anatomical feature within the medical image data 214 and analyze the anatomical feature for irregularities or abnormalities. For example, the detection and quantification module 212 may include one or more image recognition algorithms, shape or edge detection algorithms, gradient algorithms, and the like to process input medical images. Additionally or alternatively, the detection and quantification module 212 may store instructions for implementing a neural network, such as a convolutional neural network, for detecting and quantifying anatomical irregularities captured in the medical image data 214. For example, the detection and quantification module 212 may include trained and/or untrained neural networks and may further include training routines, or parameters (e.g., weights and biases), associated with one or more neural network models stored therein. In some embodiments, the detection and quantification module 212 may evaluate the medical image data 214 as it is acquired in real-time. Additionally or alternatively, the detection and quantification module 212 may evaluate the medical image data 214 offline, not in real-time.

As an example, when the medical image data 214 includes lung ultrasound data, the identified anatomical feature may include pleura, which may be identified by the detection and quantification module 212 based on pleural sliding via edge detection techniques and/or gradient changes. As will be elaborated wherein with respect to FIG. 3, once pleural positioning is detected in each frame, the detection and quantification module may score the pleura according to several parameters, including local dimness and vertical location, to determine which pleural locations are irregular.

Optionally, the image processor 231 may be communicatively coupled to a training module 210, which includes instructions for training one or more of the machine learning models stored in the detection and quantification module 212. The training module 210 may include instructions that, when executed by a processor, cause the processor to build a model (e.g., a mathematical model) based on sample data to make predictions or decisions regarding the detection and classification of anatomical irregularities without the explicit programming of a conventional algorithm that does not utilize machine learning. In one example, the training module 210 includes instructions for receiving training data sets from the medical image data 214. The training data sets comprise sets of medical images, associated ground truth labels/images, and associated model outputs for use in training one or more of the machine learning models stored in the detection and quantification module 212. The training module 210 may receive medical images, associated ground truth labels/images, and associated model outputs for use in training the one or more machine learning models from sources other than the medical image data 214, such as other image processing systems, the cloud, etc. In some embodiments, one or more aspects of the training module 210 may include remotely-accessible networked storage devices configured in a cloud computing configuration. Further, in some embodiments, the training module 210 is included in the non-transitory memory 206. Additionally or alternatively, in some embodiments, the training module 210 may be used to generate the detection and quantification module 212 offline and remote from the image processing system 200. In such embodiments, the training module 210 may not be included in the image processing system 200 but may generate data stored in the image processing system 200. For example, the detection and quantification module 212 may be pre-trained with the training module 210 at a place of manufacture.

The non-transitory memory 206 further stores the medical image data 214. The medical image data 214 includes, for example, functional and/or anatomical images captured by an imaging modality, such as an ultrasound imaging system, an MRI system, a CT system, a PET system, etc. As one example, the medical image data 214 may include ultrasound images, such as lung ultrasound images. Further, the medical image data 214 may include one or more of 2D images, 3D images, static single frame images, and multi-frame cine-loops (e.g., movies).

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories, imaging data, test results, diagnosis information, management information, and/or scheduling information, for example.

The image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a smartphone, a tablet, a smartwatch, or the like.

It may be understood that the medical image processing system 200 shown in FIG. 2 is one non-limiting embodiment of an image processing system, and other imaging processing systems may include more, fewer, or different components without parting from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200).

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
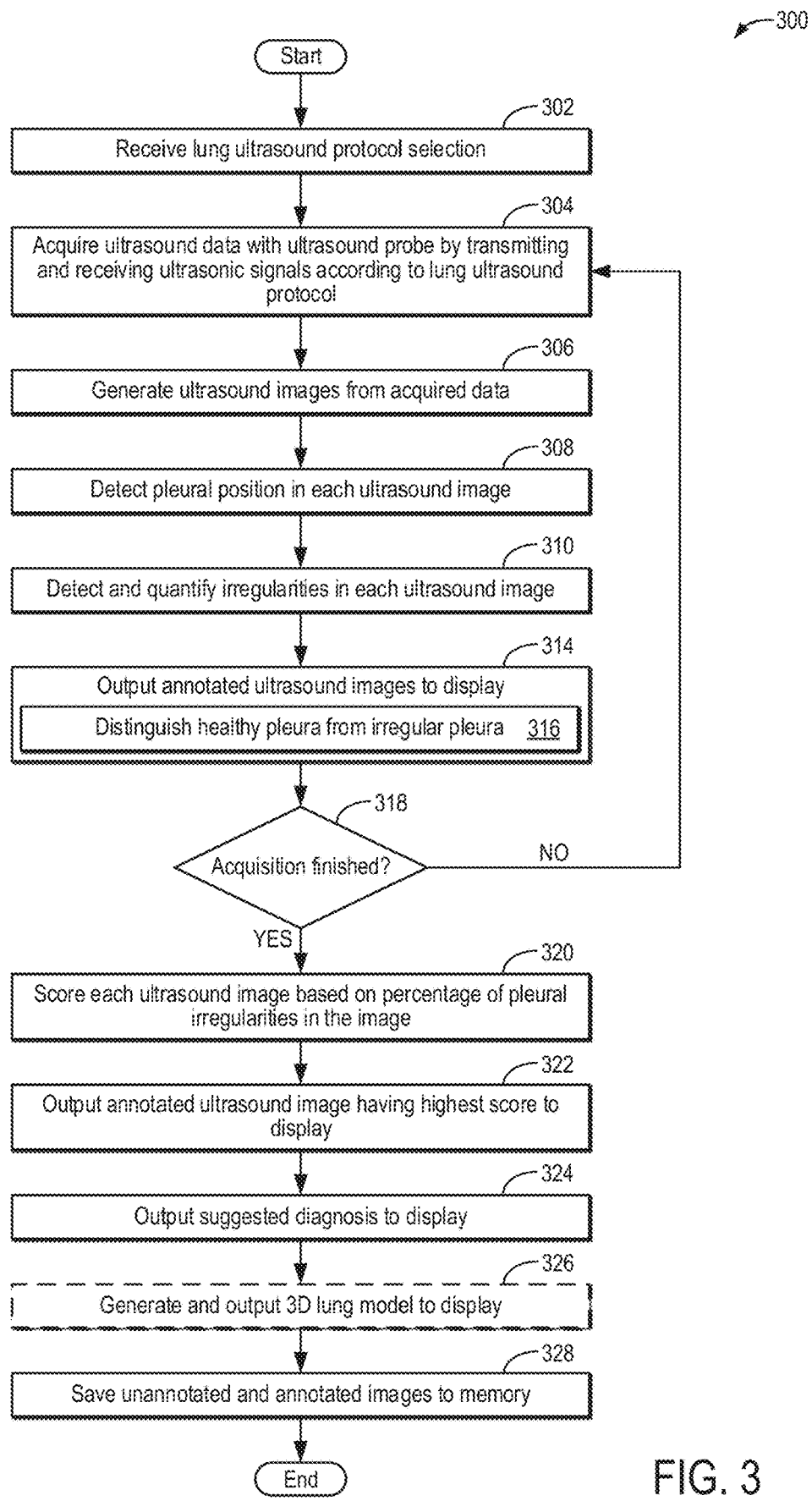
FIG. 3 shows a flow chart of an example method for detecting and quantifying pleural irregularities in real-time during a lung ultrasound, according to an embodiment.

Next, FIG. 3 shows a flow chart of an example method 300 for identifying and quantifying pleural irregularities in lung images of a patient. In particular, method 300 provides a workflow for expediting and increasing an accuracy of diagnosing the patient. Method 300 will be described for ultrasound images acquired using an ultrasound imaging system, such as ultrasound imaging system 100 of FIG. 1, although other ultrasound imaging systems may be used. Further, method 300 may be adapted to other imaging modalities. Method 300 may be implemented by one or more of the above described systems, including the ultrasound imaging system 100 of FIG. 1 and medical image processing system 200 of FIG. 2. As such, method 300 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, method 300 is performed in real-time, as the ultrasound images are acquired, while in other embodiments, at least portions of method 300 are performed offline, after the ultrasound images are acquired. For example, the processor may evaluate ultrasound images that are stored in memory even while the ultrasound system is not actively being operated to acquire images. Further still, at least parts of method 300 may be performed in parallel. For example, ultrasound data for a second image may be acquired while a first ultrasound image is generated, ultrasound data for a third image may be acquired while the first ultrasound image is analyzed, and so on.

At 302, method 300 includes receiving a lung ultrasound protocol selection. The lung ultrasound protocol may be selected by an operator (e.g., user) of the ultrasound imaging system via a user interface (e.g., the user interface 115). As one example, the operator may select the lung ultrasound protocol from a plurality of possible ultrasound protocols using a drop-down menu or by selecting a virtual button. Alternatively, the system may automatically select the protocol based on data received from an electronic health record (EHR) associated with the patient. For example, the EHR may include previously performed exams, diagnoses, and current treatments, which may be used to select the lung ultrasound protocol. Further, in some examples, the operator may manually input and/or update parameters to use for the lung ultrasound protocol. The lung ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the lung ultrasound protocol may include a plurality of scanning sites (e.g., views), probe movements, and/or imaging modes that are sequentially performed. For example, the lung ultrasound protocol may include using real-time B-mode imaging with a convex, curvilinear, or linear ultrasound probe (e.g., the probe 106 of FIG. 1). In some examples, the lung ultrasound protocol may further include using dynamic M-mode. The lung ultrasound protocol may include a longitudinal scan, wherein the probe is positioned perpendicular to the ribs, and/or an oblique scan, wherein the probe is positioned along intercostal spaces between ribs. Further still, in some examples, the lung ultrasound protocol may include a panoramic sweep, where the user sweeps the ultrasound probe from the head downward, and multiple views from the sweep may be stitched together to provide anatomical and spatial relationships. In some embodiments, the probe may include a three-dimensional probe sensor that may give width information an imaged lung, while a length of the sweep may indicate a length of the imaged lung.

At 304, method 300 includes acquiring ultrasound data with the ultrasound probe by transmitting and receiving ultrasonic signals according to the lung ultrasound protocol. Acquiring ultrasound data according to the lung ultrasound protocol may include the system displaying instructions on the user interface, for example, to guide the operator through the acquisition of the designated scanning sites. Additionally or alternatively, the lung ultrasound protocol may include instructions for the ultrasound system to automatically acquire some or all of the data or perform other functions. For example, the lung ultrasound protocol may include instructions for the user to move, rotate and/or tilt the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or ultrasound signal display parameters. Further, the acquired ultrasound data include one or more image parameters calculated for each pixel or group of pixels (for example, a group of pixels assigned the same parameter value) to be displayed, where the one or more calculated image parameters include, for example, one or more of an intensity, velocity, color flow velocity, texture, graininess, contractility, deformation, and rate of deformation value.

At 306, method 300 includes generating ultrasound images from the acquired ultrasound data. For example, the signal data acquired during the method at 304 is processed and analyzed by the processor in order to produce an ultrasound image at a designated frame rate. The processor may include an image processing module that receives the signal data (e.g., image data) acquired at 304 and processes the received image data. For example, the image processing module may process the ultrasound signals to generate slices or frames of ultrasound information (e.g., ultrasound images) for displaying to the operator. In one example, generating the image may include determining an intensity value for each pixel to be displayed based on the received image data (e.g., 2D or 3D ultrasound data). As such, the generated ultrasound images may be 2D or 3D depending on the mode of ultrasound being used (such as B-mode, M-mode, and the like). The ultrasound images will also be referred to herein as "frames" or "image frames."

At 308, method 300 includes detecting a pleural position in each ultrasound image. In an aerated lung, the pleura, which form the outer boundary of the lung that lies against the chest wall, may provide the substantially only anatomical lung structure detectable by ultrasound. The pleura appear as a hyperechoic horizontal segment of brighter (e.g., whiter) pixels in the ultrasound image, referred to as a pleural line, which moves synchronously with respiration in a phenomenon known as pleural sliding. The processor may utilize an analysis module, such as the detection and quantification module 212 of FIG. 2, to identify the horizontal (or diagonal, in some orientations) line that demonstrates the most amount of pleural sliding in order to define the pleural position (and thus the pleural line) in each image. For example, the processor may evaluate consecutive frames and identify a horizontal (or diagonal) area having a highest amount of local change between consecutive frames, such as by summing absolute differences between frames, to identify the pleural sliding and thus, the pleural position. In frames without pleural sliding (e.g., between breaths), the location of the pleura may be tracked up/down based on its known location from the previous frame.

Additionally or alternatively, detecting the pleural position may include identifying lower and upper borders of the pleura based on a brightness change between pixels, such as by using edge detection techniques or gradient changes. For example, the processor may apply an edge detection algorithm that comprises one or more mathematical methods for identifying points (e.g., pixels) at which the image brightness changes sharply and/or has discontinuities to identify the lower and upper borders of the pleural line. As one example, the processor may apply the edge detection algorithm to the area having the highest amount of local change. As another example, additionally or alternatively, a gradient algorithm may identify a local maximum and/or minimum pixel brightness at the pleural position to identify the lower and upper borders of the pleural line in each image.

At 310, method 300 includes detecting and quantifying irregularities in each ultrasound image. For example, when the air content decreases due to the presence of fluid in the lung, the ultrasound signal may be partly reflected at deeper zones than the pleura, resulting in vertical reverberation artifacts known as B-lines. As the number of B-lines increases, an air content of the lung decreases and a density of the lung increases due to scarring and/or accumulation of fluid in the pulmonary interstitial space, such as through lung consolidation. While one or two B-lines may not indicate a disease state, more than two B-lines or confluent B-lines may indicate irregularities, such as lung consolidation.

Thus, as one example, detecting and quantifying irregularities in each ultrasound image may include identifying B-lines in each ultrasound image. The processor may identify the B-lines as discrete vertical hyperechoic reverberation artifacts that move synchronously with pleural sliding, extending from the pleural line to the bottom of the image. The processor may further sum the number of B-lines found in each frame.

Detecting and quantifying the irregularities in each ultrasound image further includes detecting and quantifying pleural irregularities. For example, the processor may evaluate each pixel of the identified pleura (e.g., within the upper and lower borders of the pleural line) to locally characterize the pleura as either healthy or irregular via pre-determined scoring criteria. As an example, the processor may evaluate each pixel of the pleural line to determine a jumpiness score and a dimness score for each pleural location in order to identify positions of pleural irregularities. The jumpiness score evaluates a vertical location of the pleural line at each horizontal location to identify vertical gaps in the pleural line, with a greater vertical gap resulting in a higher jumpiness score. For example, the vertical gap may refer to a number of pixels vertically between the lower border (or upper border) of the pleural line at the given pixel location relative to a neighboring pixel. The vertical gap between the upper or lower border of the pleural line at neighboring horizontal locations may result in the pleural line having a discontinuous or rough appearance, for example. The dimness score ranks the pleural pixel brightness (or dimness) at a particular horizontal location relative to its neighbors. As the local pixel brightness of the pleura decreases relative to its neighbors (e.g., the pixel becomes more dim relative to its neighbors), the dimness score increases.

An irregularity score for each pixel along the pleural line in each frame may be generated as a product of the jumpiness score and the dimness score and compared to a threshold score. The threshold score may be a pre-determined value stored in memory that distinguishes irregular pleura associated with a disease state from normal, healthy pleura. In some examples, the threshold score may be adjusted based on curated data and using a support vector machine. If the irregularity score is greater than or equal to the threshold score, the pleura imaged in that pixel location may be considered irregular. In contrast, if the irregularity score is less than the threshold score, the pleura imaged in that pixel location may not be considered irregular (e.g., may be considered normal and/or healthy). Although the pleura may be analyzed on a pixel-by-pixel basis, a filter may be used to smooth the results. As a result, an area of pixels having pre-determined dimensions may be grouped and identified as a location of irregularity (e.g., irregular pleura) responsive to a majority (e.g., greater than 50%) of the pixels within the group being characterized as irregular pleura. In contrast, the area of pixels may be identified as healthy responsive to the majority of the pixels within the group being characterized as healthy pleura.

At 314, method 300 includes outputting annotated ultrasound images to a display. For example, the ultrasound images may comprise the pixel parameter values (e.g., brightness values) calculated at 306, and an annotated version of each ultrasound image that comprises the pixel parameter values overlaid with visual indications (e.g., annotations) regarding B-lines, the pleural position, and/or pleural irregularities may be output to the display in real-time. In some examples, the display is included in the ultrasound imaging system, such as display device 118. For example, B-lines may be highlighted with a solid vertical line, and the upper and/or lower border (e.g., boundary) of the pleural line may be indicated with markers or traced (e.g., with a line). Further, outputting the annotated ultrasound images includes distinguishing the healthy pleura from irregular pleura, as indicated at 316. As one example, healthy pleura may be visually indicated with a first marker, while irregular pleura may be visually indicated with a second marker. The first marker may be an annotation, such as a dot, square, bracket, line, or arrow, having a first characteristic (e.g., a first characteristic shape and/or color), and the second marker may be an annotation having a second characteristic that is different than the first characteristic. As another example, tissue colorization may be used to distinguish healthy pleura from irregular pleura, such as by colorizing the healthy pleura with a first color and colorizing the irregular pleura with a second, different color.

Each annotated ultrasound image may be output in substantially real-time in the sequence acquired and at a designated display frame rate.

Figure 4:
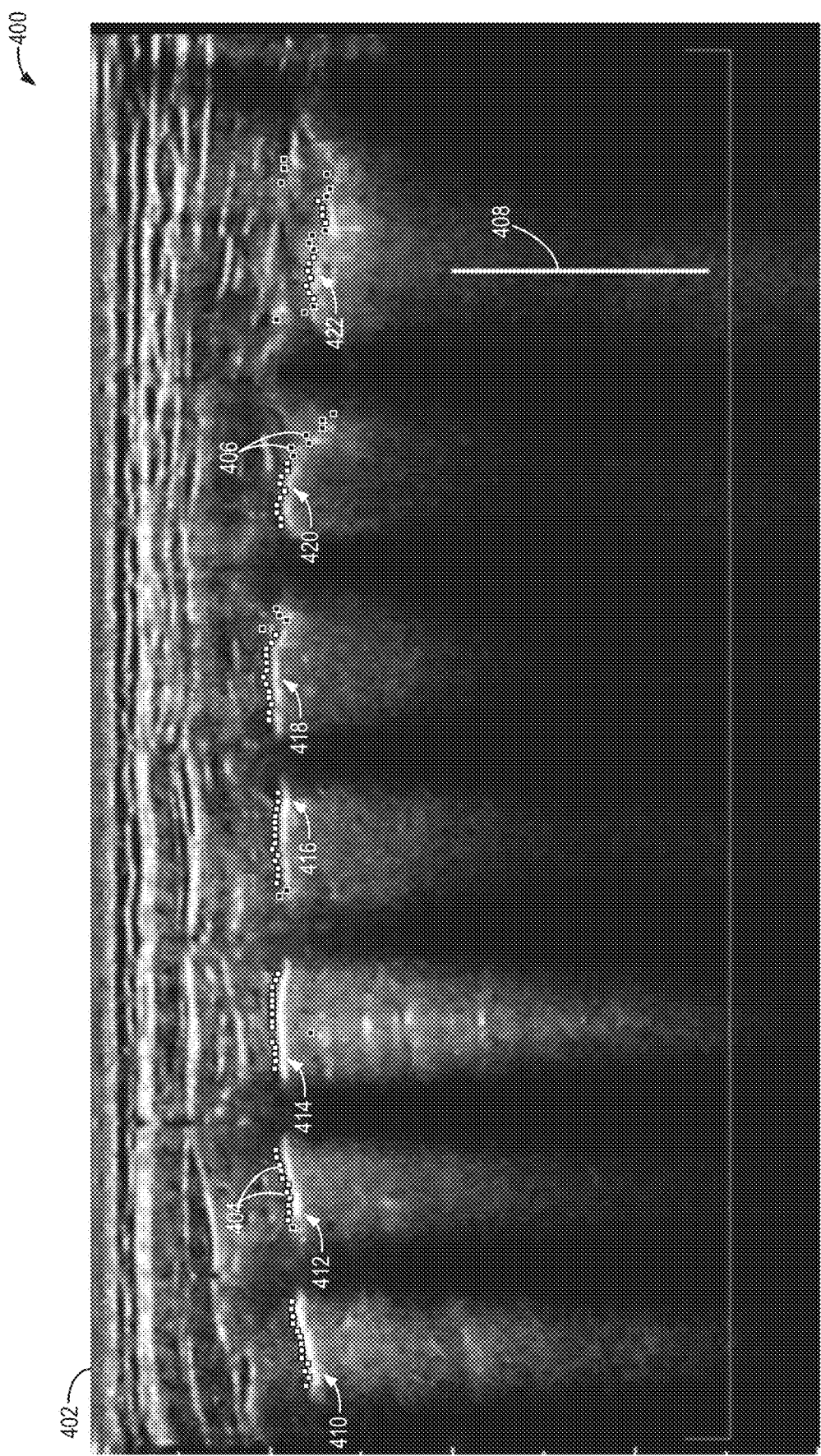
FIG. 4 shows a first example annotated panoramic lung ultrasound image that may be output to a display, according to an embodiment.

Turning briefly to FIG. 4, a first example annotated panoramic lung ultrasound image 400 that may be output to a display is shown. The first example annotated panoramic lung ultrasound image 400 includes a panoramic lung ultrasound image 402, healthy markers 404, irregular markers 406, and a B-line indicator 408. The panoramic lung ultrasound image 402 shows seven distinct pleural lines: a first pleural line 410 of a first rib space, a second pleural line 412 of a second rib space, a third pleural line 414 of a third rib space, a fourth pleural line 416 if a fourth rib space, a fifth pleural line 418 of a fifth rib space, a sixth pleural line 420 of a sixth rib space, and a seventh pleural line 422 of a seventh rib space, each pleural line separated by a dark portion in the image where a rib is located. Both the healthy markers 404 and the irregular markers 406 are positioned on an upper boundary of each pleural line in the example shown, with the healthy markers 404 visually indicating locations having healthy pleura and the irregular markers 406 visually indicating locations having pleural irregularities (e.g., as determined at 310 of FIG. 3).

In the present example, the healthy markers 404 are white squares with black outlines, while the irregular markers 406 are black squares with white outlines, although other shapes and colors are also possible. Thus, the healthy markers 404 and the irregular markers 406 have the same shape and size but different coloration. Further, the B-line indicator 408 is shown as a vertical line.

The first pleural line 410 does not have any pleural irregularities (e.g., all of the markers are the healthy markers 404). The number of pleural irregularities generally increases from the fourth pleural line 416 toward the seventh pleural line 422, with the seventh pleural line 422 having the most irregular pleura (e.g., the greatest ratio of irregular markers 406 to healthy markers 404 of the seven pleural lines). The seventh pleural line 422 also includes an identified B-line, as indicated by the B-line indicator 408. Thus, the annotated panoramic lung ultrasound image 400 shows increasing irregularities from left to right in the panoramic lung ultrasound image 402.

However, other markers are also possible to distinguish healthy pleura from irregular pleura. Turning now to FIG. 5, a second example annotated panoramic lung ultrasound image 500 that may be output to a display is shown. The second example annotated panoramic lung ultrasound image 500 includes the same panoramic lung ultrasound image 402 as in FIG. 4, and thus, components of FIG. 5 that are the same as those in FIG. 4 are numbered the same and will not be reintroduced. For example, the annotated panoramic lung ultrasound image 500 includes the same healthy markers 404 positioned above each pleural line. However, the annotated panoramic lung ultrasound image 500 includes irregular markers 506, which are shown as brackets above areas having irregular pleura, instead of the irregular markers 406. Thus, the irregular markers 506 have a different shape, color, and position than the healthy markers 404.

Returning to FIG. 3, at 318, it is determined if the acquisition is finished. For example, the acquisition may be considered finished when ultrasound data is acquired for all of the views and/or imaging modes programmed in the lung ultrasound protocol and the ultrasound probe is no longer actively transmitting and receiving ultrasonic signals. Additionally or alternatively, the acquisition may be finished responsive to the processor receiving an "end protocol" input from the operator.

If the acquisition is not finished, such as when the ultrasound probe is still actively acquiring ultrasound data according to the lung ultrasound protocol and/or there are remaining views/imaging modes in the lung ultrasound protocol, method 300 returns to 304 and continues acquiring ultrasound data with the ultrasound probe according to the lung ultrasound protocol.

Once the acquisition is finished, such as responsive to the completion of the lung ultrasound protocol, method 300 proceeds to 320 and includes scoring each ultrasound image based on a percentage (or magnitude) of pleural irregularities in the image. For example, the processor may determine the percentage of pleural locations that are identified as irregular relative to a total number of identified pleural locations. As an example, the processor may count the healthy markers and the irregular markers in each annotated ultrasound image generated during the acquisition to quantify the percentage of pleural irregularities in that image and score the image accordingly. For example, the processor may input the percentage into a look-up table stored in memory, which may output the corresponding score. As the percentage (or quantity) of pleural irregularities increases, the score increases. In some examples, the processor may further take into account a number of identified B-lines in the image, with the score further increasing as the number of identified B-lines increases. For example, the processor may input both the percentage of pleural irregularities and the number of identified B-lines into the look-up table to determine the score.

At 322, method 300 includes outputting the annotated ultrasound image having the highest score to the display. The annotated ultrasound image having the highest score may serve as a "best-frame" representation of any lung pathology present and may be output immediately following the acquiring, for example. Thus, the annotated ultrasound image having the highest score may be displayed in real-time during the acquisition and again after the acquisition is completed. In this way, the annotated ultrasound image representing the greatest quantified irregularity is displayed to the operator in order to highlight any present lung pathology. When a panoramic view is displayed, the highest scoring frame for each rib space is selected and spliced with the other highest scoring frames, forming a composite image of portions of a plurality of images acquired at different times during the lung ultrasound protocol.

At 324, method 300 includes outputting a suggested diagnosis to the display. As one example, the presence of B-lines and consolidation may indicate an accumulation of fluid, such as due to bacterial or viral pneumonia (e.g., due to COVID-19). Further, the processor may take into account a spread pattern of the irregularities among rib spaces (e.g., concentrated in a few spots or spread across the lungs). As another example, a lack of pleural sliding may indicate a collapsed lung. As such, the processor may compare the annotated ultrasound image having the highest score to a plurality of models corresponding to healthy lung or disease states and select the model having the best fit to output as the suggested diagnosis. The suggested diagnosis may be output as a text-based message alongside or overlapping the displayed highest scoring annotated image. As one example, when the best fit model is pneumonia, the message may read, "Consider pneumonia." In addition to or as an alternative to the suggested diagnosis, the processor may output suggestions on findings, such as irregular pleura, a sub-pleural consolidation, and the like.

At 326, method 300 optionally includes generating and outputting a 3D lung model to the display. For example, the 3D lung model may be generated when a lung sweep is performed during the lung ultrasound protocol. The 3D lung model may be patient-specific or may be generic. For example, the patient-specific lung model may be sized according to length and width measurements determined during the lung sweep and using a 3D probe sensor, as described above. As another example, the patient-specific 3D lung model may be generated via image fusion with a high resolution-CT dataset, a chest x-ray image, or an MR image. The 3D lung model may include one or more acquired ultrasound images overlaid on the model. As one example, the 3D lung model may include the highest scoring annotated lung ultrasound image for each view positioned at an anatomically relevant position with respect to the lungs. The 3D model may be rotatable via user input so that the operator may evaluate different views. Further, sections of lung having pathologies may be indicated over the 3D model, such as via the annotations described above at 316 or via other annotations (e.g., text-based messages).

Turning briefly to FIG. 8, an example 3D lung model 800 is illustrated, which is output to a display 801. The display 801 may be the display device 118 of FIG. 1, for example. The 3D lung model 800 includes a windpipe (e.g., trachea) 802, a left lung 804, and a right lung 806. A cropped panoramic lung ultrasound image 808 is overlaid on the left lung 804. In the example shown, the cropped panoramic lung ultrasound image 808 is contoured to the left lung 804 in order to show a more anatomical representation of the pleural spaces. Although only one panoramic lung ultrasound image is shown in the example of FIG. 8, additional panoramic lung ultrasound images may be positioned on different locations of the 3D lung model 800, such as on a back of the left lung 804, a side of the left lung 804, a front of the right lung 806, a back of the right lung 806, or a side of the right lung 806. Further, although not explicitly shown in FIG. 8, the panoramic lung ultrasound image 808 may include annotations, as described above.

Returning to FIG. 3, at 328, method 300 includes saving the unannotated and annotated images to memory (e.g., the non-transitory memory 206 of FIG. 2). Further, raw, unprocessed ultrasound data may be saved, at least in some examples. The memory may be local to the ultrasound imaging system or may be a remote memory. For example, the unannotated and annotated images may be saved and/or archived (e.g., as a structured report in a PACS system) so that they may be retrieved and used to generate an official, physician-signed report that may be included in the patient's medical record (e.g., the EHR). Method 300 may then end.

In this way, the imaging system automatically identifies and quantifies pleural irregularities in images obtained via a lung ultrasound protocol. As a result, a mental burden on the operator may be decreased. Additionally, a variability between operators in pleural irregularity detection accuracy and frequency is decreased. Overall, an accuracy of a diagnosis may be increased while an amount of time before the diagnosis is made may be decreased.

Figure 6B:
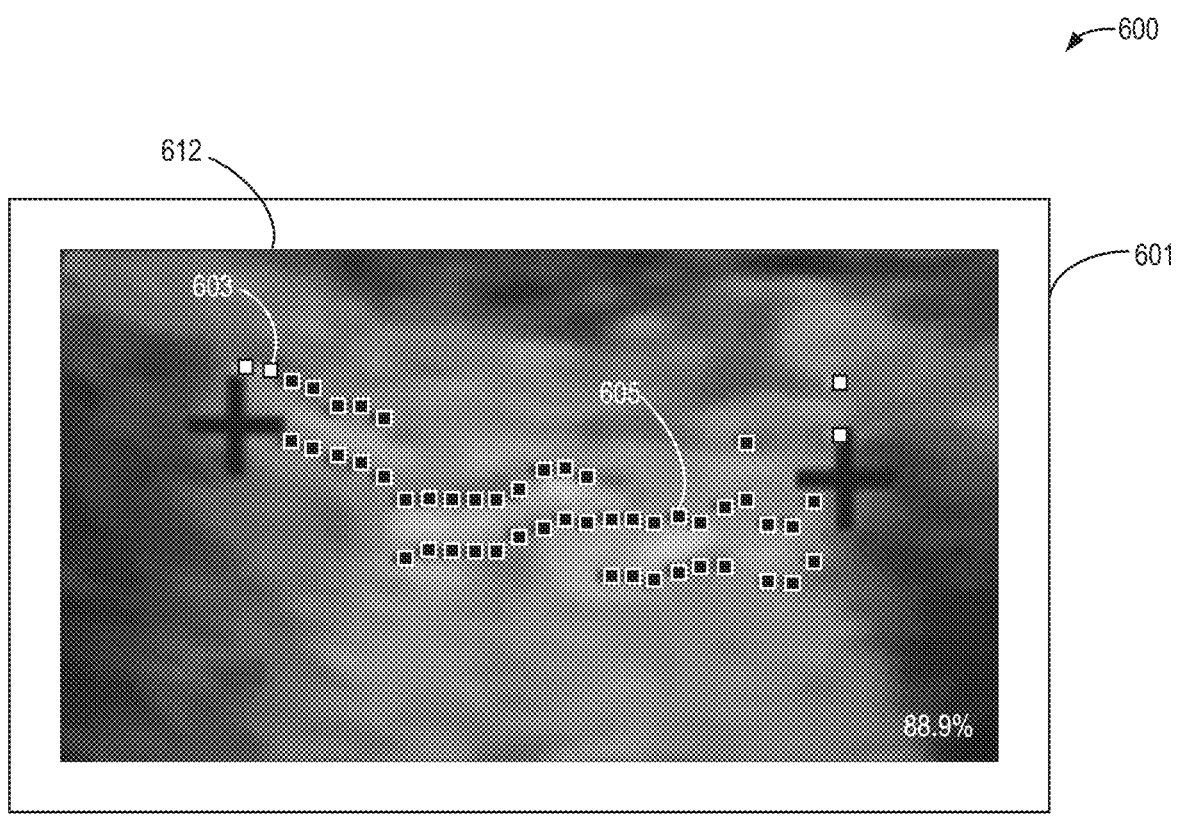

Next, FIGS. 6A and 6B show a first example sequence 600 of display outputs that may occur while acquiring lung ultrasound images (FIG. 6A) and upon completion of the acquisition (FIG. 6B). Looking first at FIG. 6A, a series of lung ultrasound images are shown with respect to a time axis 602. For illustrative clarity, each lung ultrasound image is cropped to a location around a pleural line, and the same pleural line is shown in each image (e.g., each image is acquired within the same rib space). Each lung ultrasound image is displayed on a display 601, which may be the display device 118 of FIG. 1, for example, and includes healthy markers 603 and irregular markers 605 overlaid at both the upper and lower boundaries of the imaged pleural line. The healthy markers 603 are similar to the healthy markers 404 introduced in FIG. 4, and the irregular markers 605 are similar to the irregular markers 406 of FIG. 4. Further, each displayed image includes a quantification of the percentage of pleural irregularities in that image. It may be understood that although five lung ultrasound images are included in the sequence 600, in other examples, more or fewer than five ultrasound images may be included.

A first lung ultrasound image 604 is acquired at a first time point t1, is analyzed to distinguish healthy pleura from irregular pleura (e.g., according to method 300 of FIG. 3), and is output to the display 601 in substantially real-time (e.g., substantially at time point t1). The first lung ultrasound image 604 includes 85.2% irregular pleura. A second lung ultrasound image 606 is acquired, analyzed, and output to the display 601 at a second time point t2, which occurs after the first time point t1, and has 80.8% irregular pleura. A third lung ultrasound image 608 is acquired, analyzed, and output to the display 601 at a third time point t3, which occurs after the second time point t2, and has 55.6% irregular pleura. A fourth lung ultrasound image 610 that is acquired, analyzed, and output to the display 601 at a fourth time point t4, which occurs after the third time point t3, also has 55.6% irregular pleura, although the upper and lower boundaries of the pleural line have shifted slightly relative to the third lung ultrasound image 608. A fifth and final lung ultrasound image 612 is acquired, analyzed, and output to the display 601 at a fifth time point t5 and has 88.9% irregular pleura. Following the fifth time point t5, the acquisition is finished.

Referring now to FIG. 6B, following completion of the acquisition, the fifth lung ultrasound image 612 is selected as the highest scoring image frame because it displays the highest percentage of irregular pleura of the obtained images. Thus, the fifth lung ultrasound image 612 is again output to the display 601, while the first lung ultrasound image 604, the second lung ultrasound image 606, the third lung ultrasound image 608, and the fourth lung ultrasound image 610 are not shown again on the display 601 unless specifically selected by a user (e.g., operator).

Figure 7A:
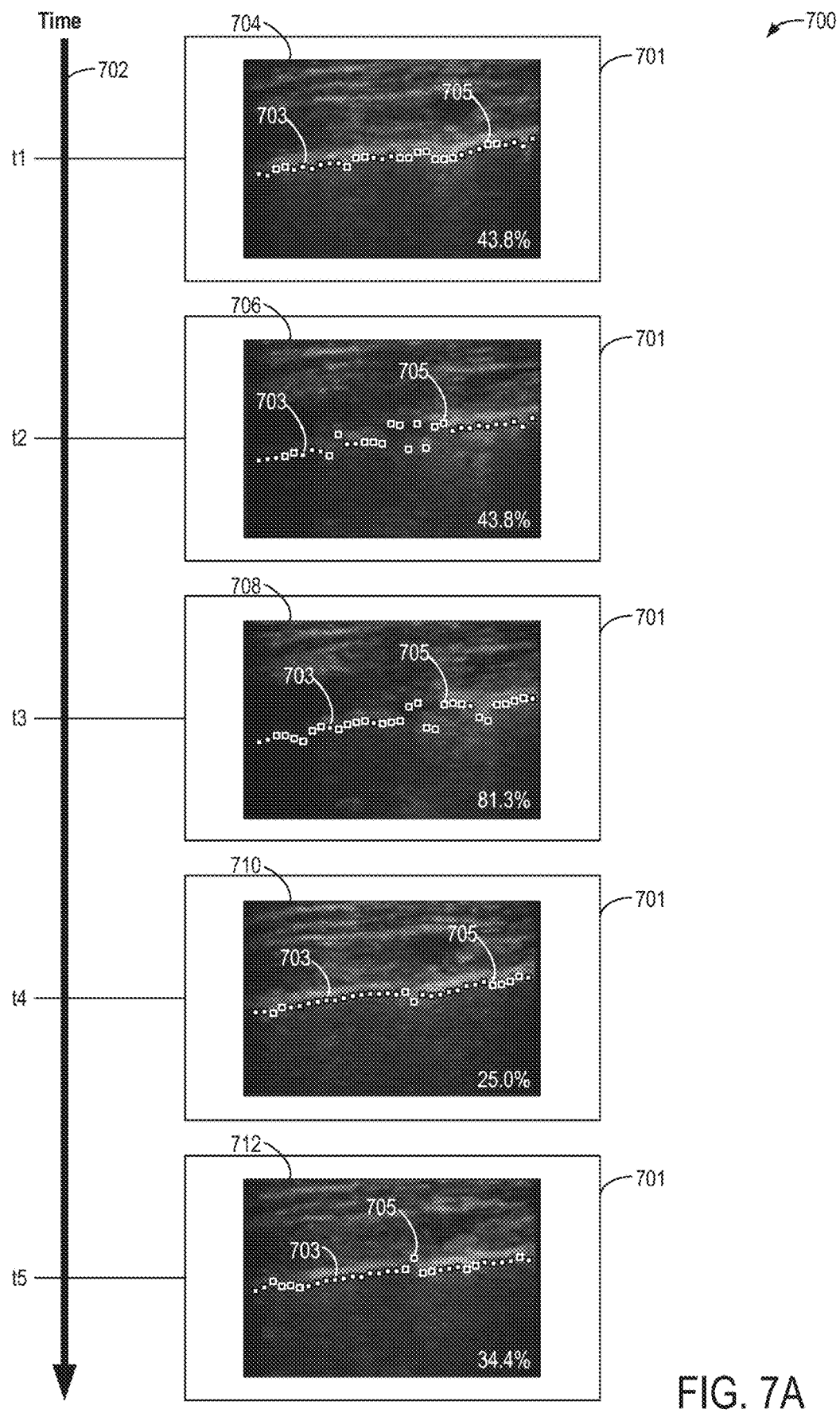
FIGS. 7A and 7B show a second example sequence of display outputs that may occur during and following a lung ultrasound, according to an embodiment.
Figure 7B:
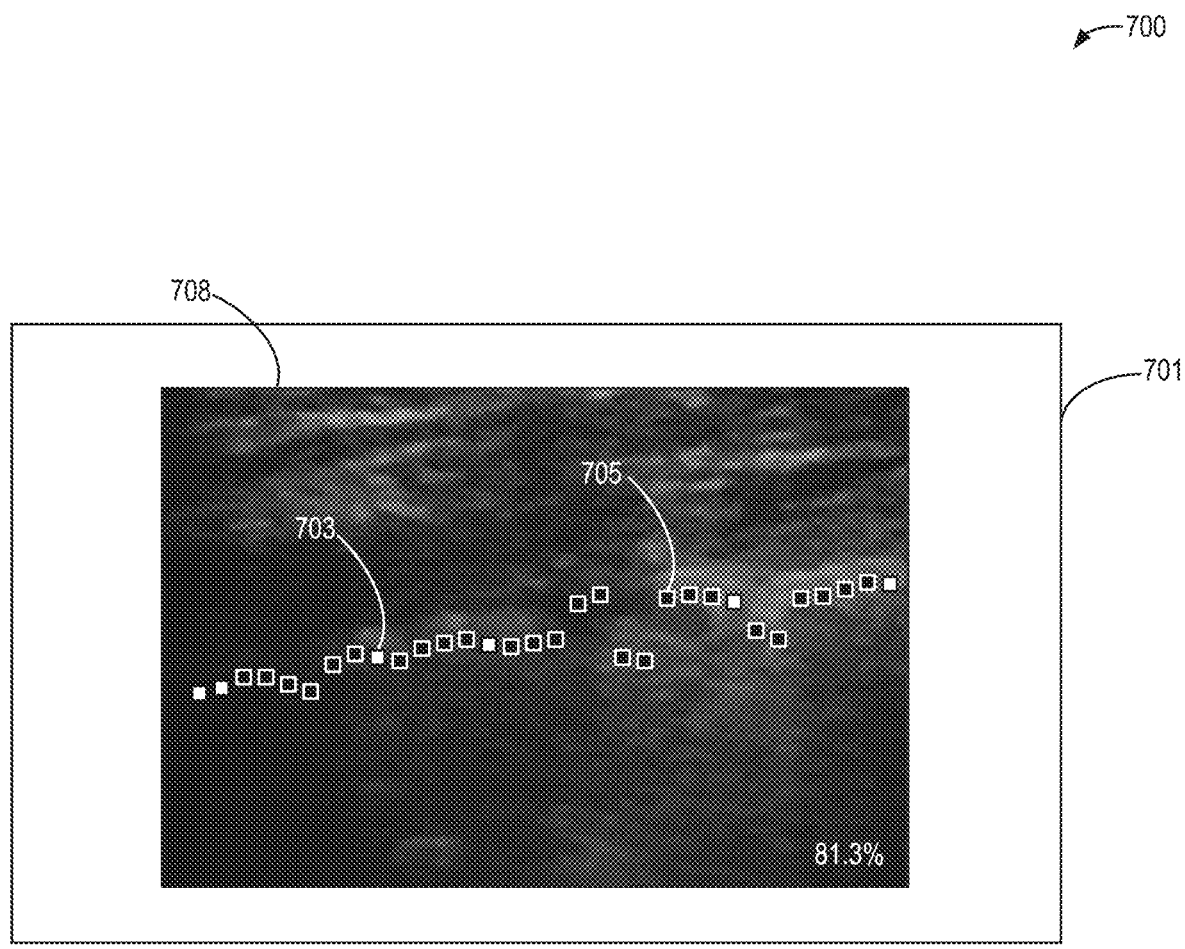
Figure 8:
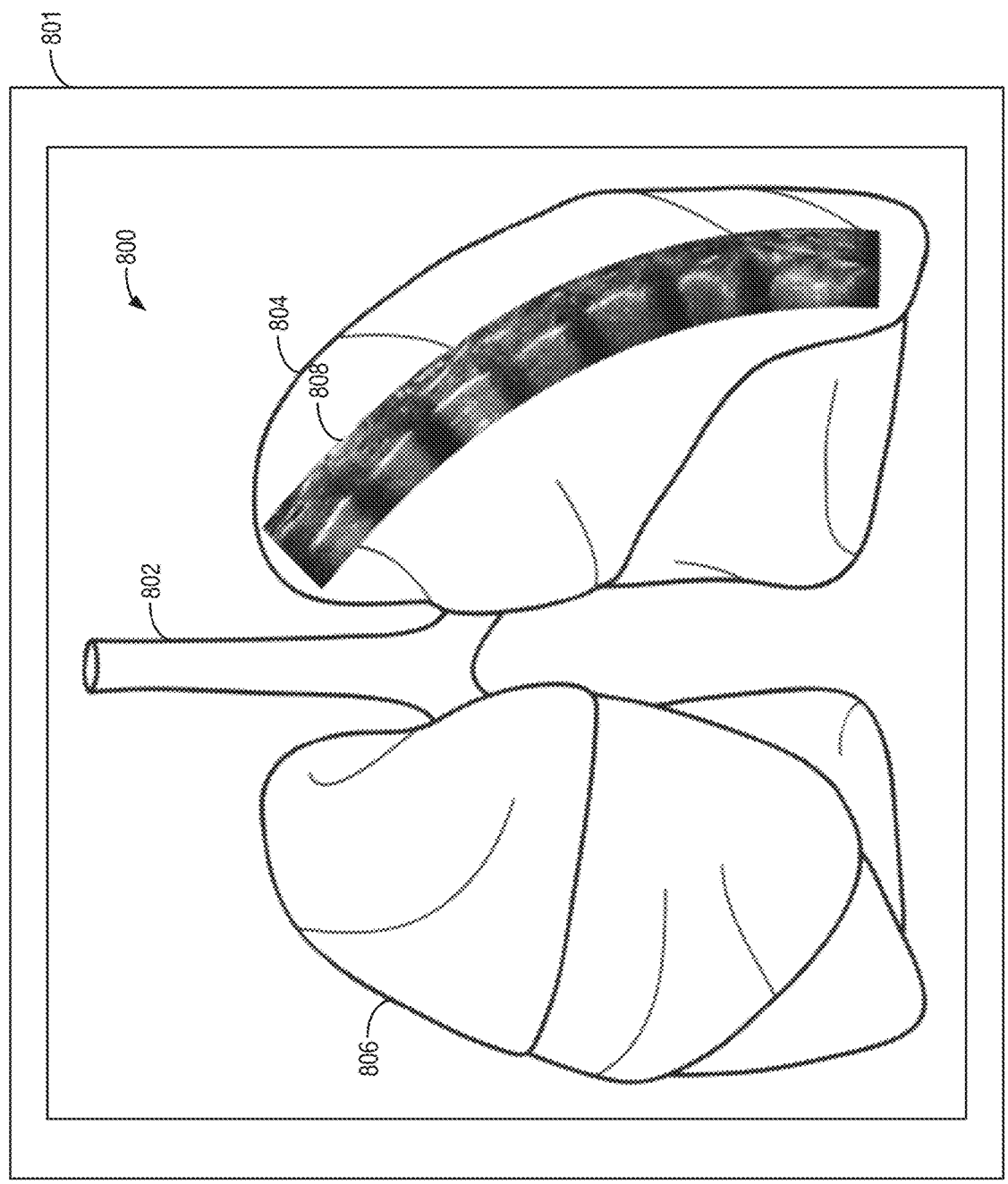
FIG. 8 shows an example three-dimensional lung model having an overlaid ultrasound image, according to an embodiment.

FIGS. 7A and 7B show a second example sequence 700 of display outputs that may occur while acquiring lung ultrasound images (FIG. 7A) and upon completion of the acquisition (FIG. 7B). Looking first at FIG. 7A, a series of lung ultrasound images are shown with respect to a time axis 702. For illustrative clarity, each lung ultrasound image is cropped to a location around a pleural line, and the same pleural line is shown in each image (e.g., each image is acquired within the same rib space). Each lung ultrasound image is displayed on a display 701, which may be the display device 118 of FIG. 1, for example, and includes healthy markers 703 and irregular markers 705 overlaid at a lower boundary of the imaged pleural line. The healthy markers 703 are similar to the healthy markers 404 introduced in FIG. 4, and the irregular markers 705 are similar to the irregular markers 406 of FIG. 4. Further, each displayed image includes an indication of the percentage of pleural irregularities in that image. It may be understood that although five lung ultrasound images are included in the sequence 700, in other examples, more or fewer than five ultrasound images may be included.

A first lung ultrasound image 704 is acquired at a first time point t1, is analyzed to distinguish healthy pleura from irregular pleura (e.g., according to method 300 of FIG. 3), and is output to the display 701 in substantially real-time (e.g., substantially at time point t1). The first lung ultrasound image 704 includes 43.8% irregular pleura. A second lung ultrasound image 706 is acquired, analyzed, and output to the display 701 at a second time point t2, which occurs after the first time point t1, and also has 43.8% irregular pleura, although the lower boundary is positioned differently than in the first lung ultrasound image 704. A third lung ultrasound image 708 is acquired, analyzed, and output to the display 701 at a third time point t3, which occurs after the second time point t2, and has 81.3% irregular pleura. A fourth lung ultrasound image 710 is acquired, analyzed, and output to the display 701 at a fourth time point t4, which occurs after the third time point t3, has 25.0% irregular pleura. A fifth and final lung ultrasound image 712 is acquired, analyzed, and output to the display 701 at a fifth time point t5, and has 34.4% irregular pleura. Following the fifth time point t5, the acquisition is finished.

Referring now to FIG. 7B, following completion of the acquisition, the third lung ultrasound image 708 is selected as the highest scoring image frame because it displays the highest percentage of irregular pleura of the obtained images. Thus, the third lung ultrasound image 708 is again output to the display 701, while the first lung ultrasound image 704, the second lung ultrasound image 706, the fourth lung ultrasound image 710, and the fifth lung ultrasound image 712 are not shown again on the display 701 unless specifically selected by a user (e.g., operator).

In this way, a processor may automatically identify and quantify pleural irregularities by evaluating medical images from a patient using one or identification and scoring algorithms. The processor may alert a healthcare professional to the detected irregularities by annotating the medical images displayed on a display device in real-time as well as outputting a suggested diagnosis and/or identified irregularities. As a result, an amount of time the healthcare professional spends reviewing the medical images may be reduced, enabling the healthcare professional to focus on patient care and comfort. Further, a "best-frame" representation of the pleural irregularities may be selected via a scoring algorithm and displayed following the acquisition, in less than real-time. Further still, by including the best-frame overlaid on a 3D rendering of a lung model, the pleural irregularities may be displayed in an anatomically relevant environment in order to further simplify a diagnostic process.

A technical effect of automatically detecting pleural irregularities in medical images is that an accuracy and frequency at which irregularities are detected may be increased.

In one embodiment, a method comprises: acquiring a series of medical images of a lung; identifying a pleural line in each medical image of the series; evaluating the pleural line for irregularities in each medical image of the series; and outputting an annotated version of each medical image of the series, the annotated version including visual markers for healthy pleura and irregular pleura. In a first example of the method, the pleural line is a substantially horizontal segment of brighter pixels, and identifying the pleural line in each medical image of the series comprises: evaluating consecutive images of the series of medical images to determine an area having a highest amount of local change between the consecutive images; and identifying an upper border and a lower border of the pleural line within the determined area based on a brightness change between pixels. In a second example of the method, which optionally includes the first example, identifying the upper border and the lower border of the pleural line is via an edge detection or gradient change algorithm. In a third example of the method, which optionally includes one or both of the first example and the second example, identifying the pleural line in each medical image of the series comprises identifying an upper border and a lower border of the pleural line based on a brightness change between pixels, and evaluating the pleural line for the irregularities comprises: determining an irregularity score for each pixel between the upper border and the lower border of the pleural line; characterizing a given pixel as healthy responsive to the irregularity score being less than a threshold score; and characterizing the given pixel as irregular responsive to the irregularity score being greater than the threshold score. In a fourth example of the method, which optionally includes one or more or each of the first through third examples, the irregularity score is a product of a first score and a second score for the given pixel. In a fifth example of the method, which optionally includes one or more or each of the first through fourth examples, the first score is determined based on a vertical gap of the pleural line at a horizontal location of the given pixel, the first score increasing as the vertical gap increases. In a sixth example of the method, which optionally includes one or more or each of the first through fifth examples, the second score is determined based on a brightness of the given pixel relative to neighboring pixels, the second score increasing as the brightness of the given pixel decreases relative to the neighboring pixels. In a seventh example of the method, which optionally includes one or more or each of the first through sixth examples, the visual markers for the healthy pleura and the irregular pleura include a first visual marker positioned at each location of the pleural line having pixels characterized as healthy and a second visual marker positioned at each location of the pleural line having pixels characterized as irregular. In an eighth example of the method, which optionally includes one or more or each of the first through seventh examples, the first visual marker includes one or more of a different shape, color, and size than the second visual marker, and one or both of the first visual marker and the second visual marker is positioned along the upper border and/or the lower border of the pleural line. In a ninth example of the method, which optionally includes one or more or each of the first through eighth examples, outputting the annotated version of each medical image of the series comprises: outputting the annotated version of each medical image of the series in real-time during the acquiring; and outputting the annotated version of one selected medical image of the series immediately following the acquiring, the one selected medical image of the series having a greatest amount of the irregular pleura relative to the healthy pleura. In a tenth example of the method, which optionally includes one or more or each of the first through ninth examples, acquiring the series of medical images of the lung includes acquiring at least one of ultrasound imaging data, magnetic resonance imaging data, computed tomography data, x-ray data, and positron emission tomography data.

In another embodiment, a method comprises: generating a plurality of lung ultrasound images while acquiring ultrasonic signals according to a protocol; visually indicating irregular pleura in each of the plurality of lung ultrasound images on a display in real-time during the acquiring; and upon completion of the protocol, selecting one image having a greatest relative amount of the irregular pleura from the plurality of lung ultrasound images and outputting only the one image to the display. In a first example of the method, visually indicating the irregular pleura in each of the plurality of lung ultrasound images on the display in real-time during the acquiring comprises: identifying borders of a pleural line in each of the plurality of lung ultrasound images based on at least pixel brightness; determining an irregularity score for each location of the pleural line; and visually distinguishing locations of the pleural line having irregularity scores less than a threshold from locations of the pleural line having irregularity scores greater than or equal to the threshold. In a second example of the method, which optionally includes the first example, the irregular pleura comprise the locations of the pleural line having the irregularity scores greater than or equal to the threshold, and determining the irregularity score for each location of the pleural line comprises: determining a first score based on a vertical gap between pleura in each location; determining a second score based on a pixel dimness of pleura in each location relative to neighboring locations; and determining the irregularity score as a product of the first score and the second score. In a third example of the method, which optionally includes one or both of the first and second examples, each of the plurality of lung ultrasound images comprises a panoramic lung ultrasound image including a plurality of rib spaces, and selecting the one image comprises: selecting separate images having the greatest relative amount of the irregular pleura for each rib space of the plurality of rib spaces; and generating the one image as a composite image using portions of the separate images selected for each rib space of the plurality of rib spaces. A fourth example of the method optionally includes one or more or each of the first through third examples and further comprises overlaying the one image on a three-dimensional lung model that is output to the display.

In yet another embodiment, a system comprises: an ultrasound probe; a display device; and a processor configured with instructions in non-transitory memory that, when executed, cause the processor to: acquire ultrasound data via the ultrasound probe according to a lung imaging protocol; generate a plurality of images from the ultrasound data; evaluate each of the plurality of images to detect pleural irregularities; and output a visual indication of the pleural irregularities on the display device in real-time. In a first example of the system, the processor is further configured with instructions in the non-transitory memory that, when executed, cause the processor to: quantify the pleural irregularities in each of the plurality of images; select one of the plurality of images having a highest quantification of the pleural irregularities; and output the selected one of the plurality of images to the display device responsive to the lung imaging protocol completing. In a second example of the system, which optionally includes the first example, the processor is further configured with instructions in the non-transitory memory that, when executed, cause the processor to: determine a suggested diagnosis based on the highest quantification of the pleural irregularities and a spacing of the pleural irregularities in the selected one of the plurality of images; and output the suggested diagnosis to the display device. In a third example of the system, which optionally includes one or both of the first and second examples, the lung imaging protocol includes a lung sweep and the ultrasound probe includes a three-dimensional sensor, and the processor is further configured with instructions in the non-transitory memory that, when executed, cause the processor to: generate a three-dimensional lung model based on a length of the lung sweep and a width measured by the three-dimensional sensor; and output the selected one of the plurality of images overlaid on the three-dimensional lung model to the display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A method, comprising:
   acquiring a series of medical images of a lung according to a lung imaging protocol;
   identifying a pleural line in each medical image of the series in real-time, while, for at least some medical images of the series, one or more additional medical images of the series are still being acquired, via a pleural position detection algorithm of an image processing system;
   detecting irregular pleura of the pleural line in each medical image of the series in real-time, while, for at least some medical images of the series, one or more additional medical images of the series are still being acquired, via at least one pixel scoring algorithm of the image processing system that scores each pixel of the pleural line based on one or more of a vertical gap of the pleural line at a horizontal location of each pixel and a brightness of each pixel relative to neighboring pixels;
   outputting an annotated version of each medical image of the series to a display in real-time, while, for at least some medical images of the series, one or more additional medical images of the series are still being acquired, the annotated version including visual markers for healthy pleura and irregular pleura positioned via algorithms of the image processing system; and
   scoring each medical image of the series based on a percentage of the irregular pleura in the pleural line via scoring algorithms of the image processing system in real-time, while, for at least some medical images of the series, one or more additional medical images of the series are still being acquired.

2. The method of claim 1, wherein the pleural line is a substantially horizontal segment of brighter pixels, and identifying the pleural line in each medical image of the series comprises:
- evaluating consecutive images of the series of medical images via the pleural position detection algorithm of the image processing system in real-time, as the consecutive images are acquired, to determine an area having a highest amount of local change between the consecutive images; and
- identifying an upper border and a lower border of the pleural line within the determined area based on a brightness change between pixels between the consecutive images via the pleural position detection algorithm of the image processing system in real-time, as the consecutive images are acquired.

3. The method of claim 2, wherein the pleural position detection algorithm of the image processing system comprises an edge detection algorithm or a gradient change algorithm, and wherein identifying the upper border and the lower border of the pleural line is via the edge detection algorithm or the gradient change algorithm.

4. The method of claim 1, wherein identifying the pleural line in each medical image of the series comprises identifying, via the pleural position detection algorithm of the image processing system, an upper border and a lower border of the pleural line based on a brightness change between pixels of consecutive images of the series of medical images, and wherein detecting irregular pleura of the pleural line via the at least one pixel scoring algorithm of the image processing system that scores each pixel of the pleural line based on one or more of the vertical gap of the pleural line at the horizontal location of each pixel and the brightness of each pixel relative to neighboring pixels comprises:
- determining, via the at least one pixel scoring algorithm of the image processing system, an irregularity score for each pixel between the upper border and the lower border of the pleural line;
- characterizing, via the at least one pixel scoring algorithm of the image processing system, a given pixel as healthy responsive to the irregularity score being less than a threshold score; and
- characterizing, via the at least one pixel scoring algorithm of the image processing system, the given pixel as irregular responsive to the irregularity score being greater than the threshold score wherein the irregularity score is based on one or more of the vertical gap of the pleural line at the horizontal location of each pixel and the brightness of each pixel relative to neighboring pixels.

5. The method of claim 4, wherein the irregularity score is a product of a first score and a second score for the given pixel.

6. The method of claim 5, wherein the first score is determined based on the vertical gap of the pleural line at the horizontal location of the given pixel, the first score increasing as the vertical gap increases, the vertical gap representing a number of pixels vertically between the lower border of the pleural line at a location of the given pixel relative to a neighboring pixel.

7. The method of claim 5, wherein the second score is determined based on the brightness of the given pixel relative to neighboring pixels, the second score increasing as the brightness of the given pixel decreases relative to the neighboring pixels.

8. The method of claim 4, wherein the visual markers for the healthy pleura and the irregular pleura include a first visual marker positioned by the image processing system at each location of the pleural line having pixels characterized as healthy and a second visual marker positioned by the image processing system at each location of the pleural line having pixels characterized as irregular.

9. The method of claim 8, wherein the first visual marker includes one or more of a different shape, color, and size than the second visual marker, and wherein one or both of the first visual marker and the second visual marker is positioned by the image processing system along the upper border and/or the lower border of the pleural line.

10. The method of claim 1, further comprising:
- outputting a highest scoring medical image of the series to the display in response to completion of the lung imaging protocol.

11. The method of claim 1, wherein acquiring the series of medical images of the lung according to the lung imaging protocol includes acquiring ultrasound imaging data, magnetic resonance imaging data, computed tomography data, x-ray data, and positron emission tomography data according to the lung imaging protocol.

12. A method, comprising:
- generating a plurality of lung ultrasound images from ultrasonic signals acquired according to a protocol;
- identifying irregular pleura in each of at least a subset of the plurality of lung ultrasound images in real-time while remaining ultrasonic signals are still being acquired according to the protocol by executing, via a processor of an image processing system, a first set of instructions stored in non-transitory memory of the image processing system to identify, via the processor, borders of a pleural line in each of the plurality of lung ultrasound images based on at least pixel brightness, determine, via the processor, an irregularity score for each location of the pleural line, and identify, via the processor, locations of the pleural line having irregularity scores greater than or equal to a threshold as the irregular pleura;
- visually indicating the irregular pleura in each of at least the subset of the plurality of lung ultrasound images on a display in real-time by executing, via the processor of the image processing system, a second set of instructions stored in the non-transitory memory of the image processing system in response to the identifying the irregular pleura; and
- upon completion of the protocol, selecting one image having a greatest relative amount of the irregular pleura from the plurality of lung ultrasound images and outputting only the one image to the display by executing, via the processor of the image processing system, a third set of instructions stored in the non-transitory memory of the image processing system in response to the completion of the protocol.

13. The method of claim 12, wherein determining the irregularity score for each location of the pleural line comprises: determining, via the processor, a first score based on a vertical gap between pleura in each location; determining, via the processor, a second score based on a pixel dimness of pleura in each location relative to neighboring locations; and determining, via the processor, the irregularity score as a product of the first score and the second score.

14. The method of claim 12, wherein each of the plurality of lung ultrasound images comprises a panoramic lung ultrasound image including a plurality of rib spaces, and selecting the one image by executing, via the processor of the image processing system, the third set of instructions stored in the non-transitory memory of the image processing system in response to the completion of the protocol comprises:

selecting, via the processor, separate images having the greatest relative amount of the irregular pleura for each rib space of the plurality of rib spaces; and generating, via the processor, the one image as a composite image using portions of the separate images selected for each rib space of the plurality of rib spaces.

15. The method of claim 12, further comprising overlaying the one image on a three-dimensional lung model that is output to the display by executing, via the processor of the image processing system, a fourth set of instructions stored in the non-transitory memory of the image processing system.

16. A system, comprising:
an ultrasound probe;
a display device; and
a processor configured with instructions in non-transitory memory that, when executed, cause the processor to:
  acquire ultrasound data via the ultrasound probe according to a lung imaging protocol;
  generate a plurality of images from the ultrasound data in real-time, while at least some ultrasound data are still being acquired;
  evaluate each of the plurality of images to detect irregular pleura of a pleural line in real-time, while, for at least some images of the plurality of images, ultrasound data are still being acquired, the evaluation performed via at least one pixel scoring algorithm that scores each pixel of the pleural line based on a vertical gap of the pleural line at the horizontal location of each pixel and a brightness of each pixel relative to neighboring pixels;
  quantify the irregular pleura in each of the plurality of images in real-time, as the ultrasound data are acquired while, for at least some images of the plurality of images, ultrasound data are still being acquired; and
  output a visual indication of the irregular pleura on the display device in real-time, while, for at least some images of the plurality of images, ultrasound data are still being acquired.

17. The system of claim 16, wherein the processor is further configured with instructions in the non-transitory memory that, when executed, cause the processor to:
  select one of the plurality of images having a highest quantification of the irregular pleura responsive to the lung imaging protocol completing; and
  output the selected one of the plurality of images to the display device responsive to the lung imaging protocol completing.

18. The system of claim 17, wherein the processor is further configured with instructions in the non-transitory memory that, when executed, cause the processor to:
  determine a suggested diagnosis based on the highest quantification of the irregular pleura and a spacing of the irregular pleura in the selected one of the plurality of images; and
  output the suggested diagnosis to the display device.

19. The system of claim 17, wherein the lung imaging protocol includes a lung sweep and the ultrasound probe includes a three-dimensional sensor, and the processor is further configured with instructions in the non-transitory memory that, when executed, cause the processor to:
  generate a three-dimensional lung model based on a length of the lung sweep and a width measured by the three-dimensional sensor as the ultrasound data are acquired; and
  output the selected one of the plurality of images overlaid on the three-dimensional lung model to the display device responsive to the lung imaging protocol completing.

* * * * *